(12) United States Patent
Koza et al.

(10) Patent No.: US 11,771,506 B2
(45) Date of Patent: Oct. 3, 2023

(54) METHOD AND SYSTEM FOR CONTROLLING DENTAL MACHINES

(71) Applicant: DENTSPLY SIRONA Inc., York, PA (US)

(72) Inventors: André Koza, Worms (DE); Ronny Kucharczyk, Worms (DE)

(73) Assignee: DENTSPLY SIRONA INC., York, PA (US)

( * ) Notice: Subject to any disclaimer, the term of this patent is extended or adjusted under 35 U.S.C. 154(b) by 279 days.

(21) Appl. No.: 17/427,264

(22) PCT Filed: Jan. 27, 2020

(86) PCT No.: PCT/EP2020/051872
§ 371 (c)(1),
(2) Date: Jul. 30, 2021

(87) PCT Pub. No.: WO2020/156976
PCT Pub. Date: Aug. 6, 2020

(65) Prior Publication Data
US 2022/0142722 A1    May 12, 2022

(30) Foreign Application Priority Data
Jan. 30, 2019   (EP) ..................................... 19000055

(51) Int. Cl.
*A61B 34/00*   (2016.01)
*A61C 1/00*    (2006.01)
*G06F 3/01*    (2006.01)
*G06F 3/033*   (2013.01)
*G06F 3/04815* (2022.01)
*G06T 19/00*   (2011.01)

(52) U.S. Cl.
CPC ............ *A61B 34/25* (2016.02); *A61C 1/0023* (2013.01); *G06F 3/011* (2013.01); *G06F 3/0334* (2013.01); *G06F 3/04815* (2013.01); *G06T 19/006* (2013.01); *G06T 2200/24* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 10,424,115 B2 * | 9/2019 | Ellerbrock | H04N 5/32 |
| 2019/0371028 A1 * | 12/2019 | Harrises | G06T 11/60 |
| 2021/0121246 A1 * | 4/2021 | Gudalo | G06T 7/73 |

* cited by examiner

*Primary Examiner* — Nicholas J Lee
(74) *Attorney, Agent, or Firm* — DENTSPLY SIRONA INC.

(57) ABSTRACT

A method, system and a computer readable storage media for operating dental machines through an augmented reality control interface A hands free interface may enable the control of a dental machine during dental treatment by using dexterous parts of the body other than the upper limbs (e.g. by using the lower limbs) on a first user/control interface to send instructions corresponding to a second user/control interface that is different from the first user/control interface.

9 Claims, 4 Drawing Sheets

METHOD AND SYSTEM FOR CONTROLLING DENTAL MACHINES

CROSS-REFERENCE TO RELATED APPLICATIONS

This is a National Phase application of International Application No. PCT/EP20201051872, filed Jan. 27, 2020, which claims the benefit of and priority to EP Application Ser. No. 19000055.4, filed on Jan. 30, 2019, which are herein incorporated by reference for all purposes.

TECHNICAL FIELD OF THE INVENTION

The present application generally relates to a method, a system and a computer readable storage media for controlling machines and, more particularly, to a method, system and a computer readable storage media for utilizing an augmented reality control/user interface to operate dental machines such as a treatment unit.

BACKGROUND OF THE INVENTION

A user or control interface, may be defined as the space where interactions between humans and machines occur. This may allow the control of the machine from a human end. Generally, the purpose of a user interface design may be to make it easy, efficient, and user-friendly to operate a machine in a way which produces a desired result. Common user interfaces include graphical user interfaces, gesture interfaces, hardware interfaces, tangible user interfaces, text-based user interfaces, voice-controlled user interfaces.

In dentistry, a clinician may use a user/control interface of a computer, for example, to create a treatment plan, view patient radiographs, facilitate a scanning procedure etc. However during dental treatment, the clinician may need the use of his/her hands for conducting treatment procedures on a patient. For example, a clinician wearing gloves and treating a patient may have his/her gloves come into contact with the saliva/blood of a patient and may not want to contaminate a computer mouse in order to navigate programs on a computer screen. Augmented Reality (AR) glasses may be used to solve this problem. However, current AR glasses may work via a touch interaction, for example, through a touch pad on a side of the AR glasses, a voice command or a gesture using the hands. During treatment, the clinician may need his hands to conduct treatment procedures and as such controlling the AR glasses via hand gestures may hinder the treatment process. A touch interaction on a side of the pair AR glasses may also not be ideal as the AR glasses may subsequently need to be disinfected. Even further dental offices may often be loud due to, for example, treatment noise from dental machines, thereby reducing the effectiveness of voice commands for AR glasses. Therefore, there is a need for a way to control a first user interface normally controlled by the upper limbs/hands through a second user interface normally controlled by another dexterous part of the body other than the upper limbs.

US Patent Application Publication No. 20160033770A1 describes a head-mounted display device that enables a user to visually recognize a virtual image and an external scene.

US Patent Application No. 2017202633 discloses an imaging and display system for guiding medical interventions comprising a wearable display for viewing by a user wherein the display presents a composite, or combined image that includes pre-operative surgical navigation images, intraoperative images, and in-vivo microscopy images or sensing data. A probe, such as a microscopy probe or a sensing probe, may be used to acquire in-vivo imaging/sensing data from the patient and the intra-operative and in-vivo images may be acquired using tracking and registration techniques to align them with the pre-operative image and the patient to form a composite image for display.

US Patent Application No. 20020082498 discloses a method for image-guided surgery comprising capturing 3-dimensional (3D) volume data of a portion of a patient, processing the volume data so as to provide a graphical representation of the data, capturing a stereoscopic video view of a scene including a portion of said patient, rendering the graphical representation and the stereoscopic video view in a blended manner so as to provide a stereoscopic augmented image, and displaying said stereoscopic augmented image in a video-see-through display.

US Patent Application Publication No. 20160191887 describes a real-time surgery navigation method and apparatus for displaying an augmented view of a patient from a static or dynamic viewpoint of a surgeon. A surface image, a graphical representation the internal anatomic structure of the patient processed from preoperative or intraoperative images, and a computer geometrically registering both images may be used. Responsive to geometrically registering the images, a head mounted display may present to a surgeon an augmented view of the patient.

SUMMARY OF THE INVENTION

Existing limitations associated with the foregoing, as well as other limitations, can be overcome by the method according to claim 1, the system according to claim 5 and the computer readable storage media according to claim 9 for the controlling a machine.

In an aspect herein, the present invention provides a method utilizing augmented visualization, the method comprising: providing a first user interface; providing a second user interface different from the first user interface; providing an augmented reality user interface corresponding to the second user interface, the first user interface being adapted to transmit one or more control signals corresponding to the augmented reality user interface; and controlling the second user interface through the one or more control signals of the first user interface.

In another aspect herein, the method further comprises one or more of the following steps: (i) further comprising overlaying the augmented reality user interface on the first user interface such that one or more augmented reality control elements of the augmented reality user interface correspond to one or more first control elements of the first user interface or to one or more positions of a first control element of the first user interface and such that the augmented reality user interface appears directly superimposed on the first user interface, (ii) wherein the one or more augmented reality control elements of the augmented reality interface also correspond to one or more second control elements of the second user interface, (iii) wherein the one or more second control elements include, action items, software applications, videos and/or, images, (iv) further comprising operating the first user interface in a hands-free manner, (v) further comprising; updating the augmented reality user interface based on data selected from the group consisting of (a) real time data tracking clinician movements (b) real time data tracking a location of the first user interface and (c) one or more control signals of the first user interface, (vi) wherein the first user interface is a footswitch or a disinfectable control panel.

In a further aspect herein, a system utilizing augmented visualization is provided, the system comprising: a display device for augmented visualization; a first user interface; a second user interface different from the first user interface; and at least one processor configured to perform the steps of; providing an augmented reality user interface corresponding to the second user interface, the first user interface being adapted to transmit one or more control signals corresponding to the augmented reality user interface; and controlling the second user interface through the one or more control signals of the first user interface.

In yet another aspect herein, the system further comprise one or more of the following configuration: (i) further comprising a tracking system configured to offer real-time position data for a precise location and orientation of objects in a common coordinate system, (ii) wherein the tracking system is sensor based and/or vision based, (iii) wherein the first user interface is a footswitch or a disinfectable control panel. (iv) wherein the processor is further configured to perform the step of: overlaying the augmented reality user interface on the first user interface such that one or more augmented reality control elements of the augmented reality user interface correspond to one or more first control elements of the first user interface or to one or more positions of a first control element of the first user interface and such that the augmented reality user interface appears directly superimposed on the first user interface, (v) wherein the one or more augmented reality control elements of the augmented reality interface also corresponds to the one or more second control elements of the second user interface, (vi) wherein the one or more second control elements include, action items, software applications, videos and/or, images, (vii) wherein the processor is further configured to perform the step of: operating the first interface in a hands free manner, (viii) wherein the processor is further configured to perform the step of: updating the augmented reality user interface based on data selected from the group consisting of (i) real time data tracking clinician movements (ii) real time data tracking a location of the first user interface and (iii) one or more control signals of the first user interface, (ix) wherein the first user interface is a footswitch or a disinfectable control panel.

In yet another aspect herein, a non-transitory computer-readable storage medium storing a program which, when executed by a computer system, causes the computer system to perform a procedure is provided, the procedure comprising: providing an augmented reality user interface corresponding to a second user interface, receiving one or more control signals from a first user interface, said control signals corresponding to the augmented reality user interface; and controlling the second user interface through the one or more control signals of the first user interface.

BRIEF DESCRIPTION OF THE DRAWINGS

Example embodiments will become more fully understood from the detailed description given herein below in combination with the accompanying drawings, wherein.

DETAILED DESCRIPTION OF THE INVENTION

In accordance with example aspects described herein, a method, system and computer readable storage media may be provided for operating machines such as dental machines through an augmented reality user/control interface. An augmented reality interface may enable the control of a dental machine (such as a treatment unit operated with a mouse) during dental treatment by using dexterous parts of the body other than the upper limbs (e.g. by using the lower limbs) on a first user/control interface (such as a footswitch) to send instructions corresponding to a second user interface (such as a graphical user interface) wherein the first user interface is different from the second user interface. The first user/control interface may preferably be hands-free but may also involve the use of the hands in an embodiment in which that first user/control interface is capable of being disinfected.

Augmented Reality Visualization System for Controlling a Machine

Figure 1:
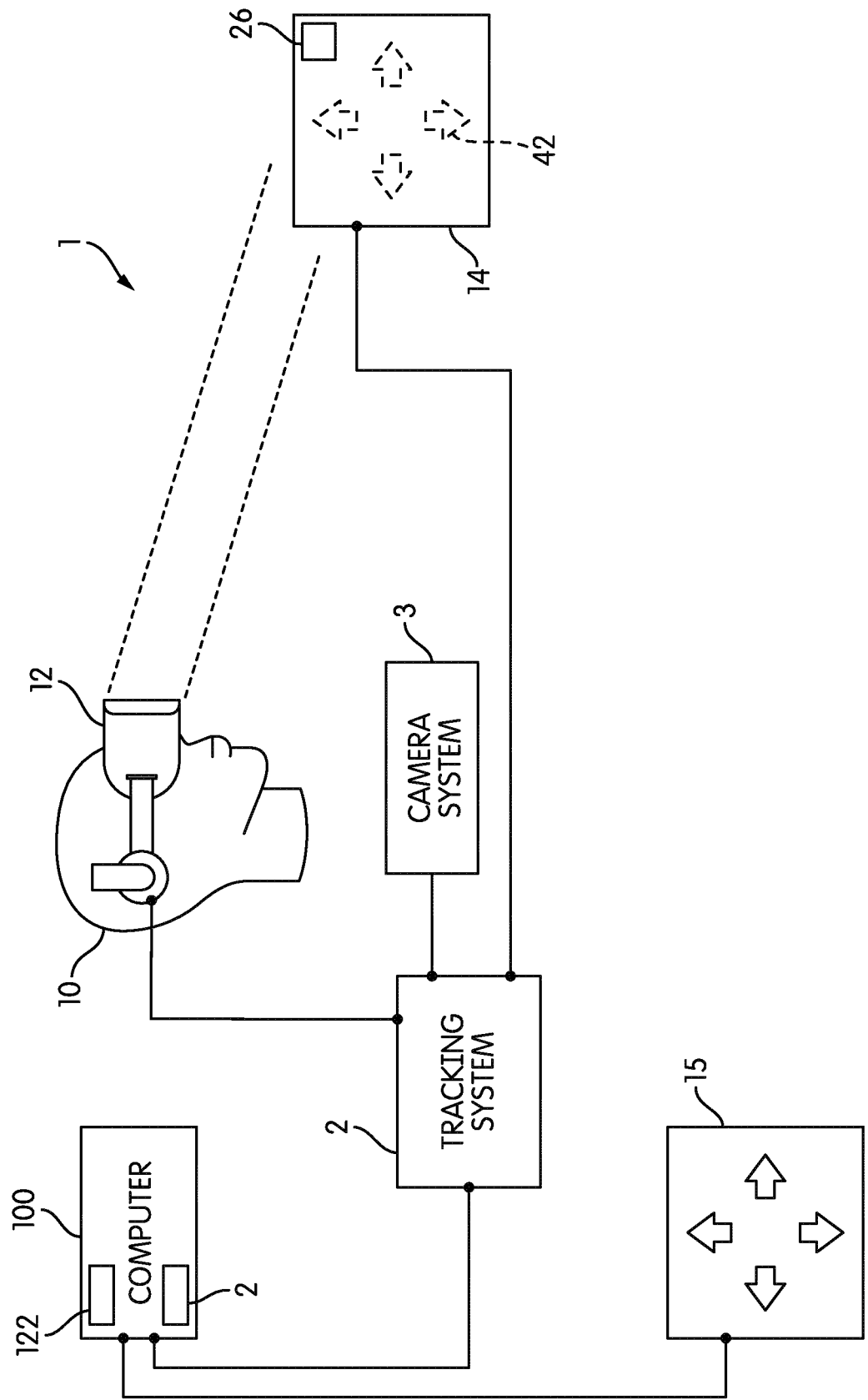
FIG. 1 is a block diagram illustrating a user interface visualization system according to an embodiment of the present invention.

FIG. 1 illustrates an augmented reality visualization system 1 comprising a display device 12 for augmented visualization such as (i) head mounted augmented reality glasses, (ii) an HUD display, or (iii) a stereoscopic display capable of receiving stereoscopic video images, or otherwise display device 12 that may be used for overlaying an augmented reality user interface 42 on a (i) first user interface 14 (which may preferably be a hardware user interface), or on (ii) a stereoscopic video/projection of the first interface 14 (said stereoscopic video/projection being viewed through the display device 12) such that the augmented reality user interface 42 appears to be directly superimposed on first user interface 14. Herein, the augmented reality user interface 42 may be configured to correspond to a second user interface 15 and the second interface 15 may be controlled through the first interface 14. The second interface may preferably be a graphical user interface (GUI) that is normally operated with the upper limbs such as, for example, a graphical user interface of a standalone computer used by a clinician 10 for viewing X-ray images, a graphical user interface of a monitor connected to a dental treatment chair, a control panel of a dental treatment chair etc. Of course, the second user interface 15 may be any other kind of user interface other than a GUI.

As discussed above, the first user interface 14 may be a footswitch 16 or any user interface capable of being controlled by the lower limbs such that the clinician 10 may be free to use his/her upper limbs on a patient (not shown) during treatment and/or such that the clinician 10 may not infect the first user interface 15 with his/her upper limbs during treatment. Examples of footswitches 16 are disclosed in U.S. Patent Application Publication No. 2014/0017629A1, entitled "Hard-Wired and Wireless System with Footswitch for Operating a Dental or Medical Treatment Apparatus", by Lint et al, and German Patent No. "DE102007014785B4", entitled "Foot Control Device" by Pabst et al, and are incorporated by reference herein in their entirety, as if set forth fully herein. In another embodiment of the present invention, however, the first user interface 14 may be a disinfectable user interface such as a control panel of a dental treatment chair and may be controlled using the upper limbs.

By projecting the augmented reality interface 42 corresponding to the second user interface 15 onto the first user interface 14, the clinician 10 may control functions of the second user interface 15 through the "more convenient" first user interface 14 and still be able to simultaneously use his/her upper limbs for treatment purposes. Moreover the clinician may benefit from using a technology he is familiar with (first user interface 14) in controlling a new application he/she may not be familiar with (second user interface 15).

As shown in FIG. 1, the display device 12 may be connected to or form part of a computer system 100. The computer system 100 (also shown in FIG. 3) may include a tracking system 2 and a processor 122. The tracking system 2 may alternatively be separate from the computer system and may form at least part of any of the devices, components, and/or systems discussed herein. The tracking system 2 may be electrically connected to a processor 122 and may offer real-time location data for a precise location and orientation of objects (such as the first user interface 14) and the clinician in a common coordinate system. In an exemplary embodiment herein, the tracking system 2 may be sensor based e.g. as embedded sensors 26 or markers (not shown) in the first user interface 14/footswitch 16 (FIG. 2), including sensors such as, for example, pressure, touch, proximity, rotational, gyroscopic sensors and global positioning system (GPS), to track the position of the footswitch 16 and/or to track output/control signals of the footswitch 16, and/or as gyroscopes or accelerometers to track the movement of the clinician 14.

The tracking system 2 may also be vision based, for example as cameras for visual tracking of the location of the first user interface 14 and/or predetermined markers (not shown) placed on the first user interface 14. Said visual tracking may be achieved using, for example object/pattern recognition. A camera system 3 such as a 3D optical tracking system and/or stereoscopic camera system may be included in the computer system and/or may form or be a part of the tracking system 2. The camera system 3 may also be embedded in the display device 12 of the clinician 10. The camera system may operate under one of several depth sensing principles in order to track a location of the first user interface 14 relative to the moving clinician 10 and vice versa in order to display the augmented reality user interface 42 on the first user interface 14 despite relative movements between the clinician 10 and the first user interface 14. The depth sensing principles may include, for example, (i) structural light, (ii) Time of Flight (ToF) and/or (iii) stereoscopic principles explained hereinafter. For cameras employing structural light, a light source may be used to project a known pattern onto the first user interface 14, and a receiver may detect the distortion of the reflected pattern to calculate a depth map based on geometry. For cameras employing Time of Flight (ToF) principles, a light source may send out a pulse toward the first user interface 14, and a sensor may detect a reflection of the pulse from the first user interface 14 in order to record it's time of flight. Knowing the time of flight and the constant speed of light, the system may calculate how far away the first user interface is. Alternatively, a modulated light source may be sent and a phase change of light reflected from the first user interface 14 may be detected. For cameras employing stereoscopic principles, multiple cameras may be placed at different positions to capture multiple images of the first user interface, and a depth map may be calculated based on geometry. This depth information may be used to track the location of first user interface 14 during treatment (e.g. during dental treatment).

In yet another embodiment, the tracking system 2 may be a fusion of sensor based tracking system and a vision based tracking system. A wireless protocol may be used to transmit data between the computer system 100 and internal/external devices such as the first user interface.

The processor 122 may be configured to receive real time tracking data, to analyze said data and to display the augmented reality user interface 42 to the clinician 10 in an augmented manner by (i) overlaying the augmented reality user interface 42 on the first user interface 14 or on a vicinity of the first user interface through the display device 12 or (ii) overlaying the augmented reality user interface 42 on a stereoscopic video of the first user interface 14 using e.g. a head mounted stereoscopic display capable of showing stereoscopic videos. Alternatively the augmented reality user interface 42 may be directly projected onto the first interface 14 using projection based augmented reality systems such that the projected augmented reality user interface 42 may be viewed with the naked eye.

Figure 2:
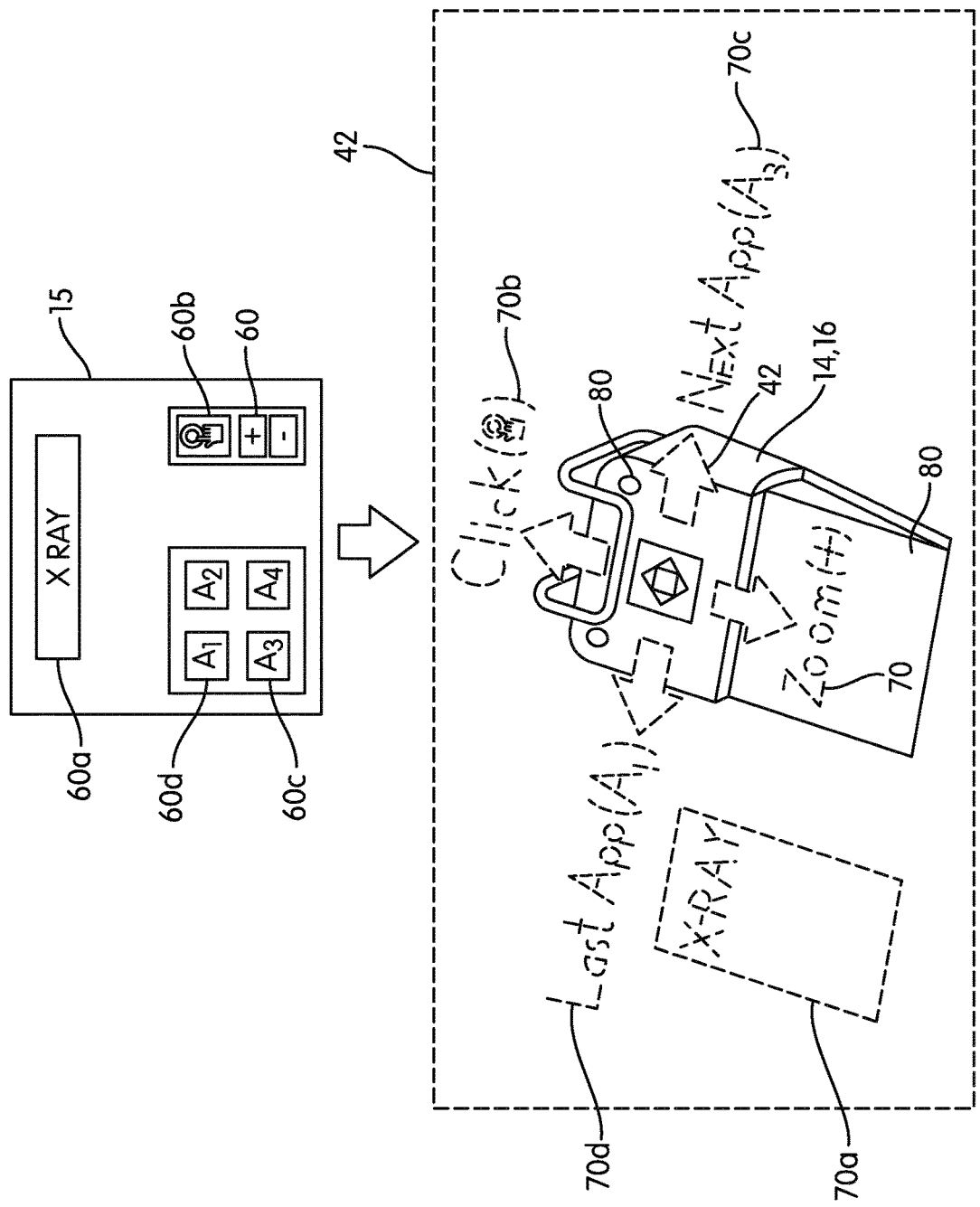
FIG. 2 illustrates a relationship between a computer display and a footswitch according to an exemplary embodiment of the present invention.

Turning now to FIG. 2, correspondences between augmented reality control elements 70 (shown in dashed lines for illustration purposes) of the augmented reality interface 42 and second control elements 60 the second user interface 15 will now be described in further detail. In using the augmented reality visualization system 1 described herein, the clinician 10 may control the second user interface 15 during a treatment procedure by selecting, (using the first user interface 14), as shown in FIG. 2, an augmented reality control element 70 displayed in the augmented reality interface 42 corresponding to a second control element 60 displayed in the second user interface 15. The augmented reality control element 70 may be selected by, for example engaging a first control element 80 (e.g. pedal of a footswitch 16, button of a disinfectable control panel, etc.) of the first user interface 14, or turning the first control element 80 to a corresponding first position in the case of e.g. a four way footswitch. The second control elements 60 in the second user interface may include, for example, action buttons/items (select, zoom, scroll, magnify etc.), software applications (e.g. performing a scanning procedure in multiple guided steps), video/image viewing panels (e.g. for viewing 3D images, X-ray images, scrolling through images etc.), and the like. The augmented reality control elements 70 may therefore be configured to correspond to the second control elements 60. As shown in the exemplary embodiment of FIG. 2, control elements 60*a*, 60*b*, 60*c* and 60*d* in the second interface 15 correspond respectively to control elements 70*a*, 70*b* and 70*c*, 70*d* of the augmented reality user interface 42 and may be controlled by one or more first control elements 80 of the first interface or one or more positions of a first control element 80 of the first user interface 14 (e.g. a disinfectable control panel acting as a first user interface may have a plurality of first control elements 80 and a footswitch 16 may have a pedal and/or a control element capable of being engaged and placed in a plurality of positions corresponding to a plurality of output/control signals).

In an embodiment wherein the second control element 60 is a video or image, the second control element 60 may be routed to the display 12 and for viewing by the clinician 10 in any position and/or may be viewed directly on the second user interface 15. In both cases the second control element 60 may be manipulated (such as edited, scrolled through, zoomed in/out of etc.) using the first control element(s) 80 of the first interface 14.

Overlaying of the augmented reality user interface 42 on the first user interface 14 may be performed dynamically and in real time and may be achieved by the processor 122 working in tandem with the tracking system 2 wherein changes in position of (i) the clinician 10 and/or (ii) the first user interface 14, captured by the tracking system 2, may be translated into corresponding changes in positions of the overlaid augmented reality user interface 42 such that said augmented reality user interface 42 routed to a screen of the display device 12 appears directly superimposed on the first user interface 14 even as the clinician 10 moves and/or first user interface changes position.

Moreover, responsive to an engagement of the first control element(s) 80 of the first user interface 14 by the clinician 10 the processor 122 may be configured to receive one or more output/control signals from the first user interface 14 and alter second user interface 15 from a first state to a second state corresponding to the output/control signal and/or alter the augmented reality user interface 42 from another first state to another second state corresponding to said output/control signal. For example, in response to the clinician 10 engaging the footswitch 16 in a first position to select augmented reality control element 70c ("→Next App ($A_3$)") the processor 122 may display contents of $A_3$ on a display of the second user interface 15 for viewing. Contents of $A_3$ may be controlled (such as clicked on or zoomed in) by using the footswitch 16 to select control elements 70b (Click) and/or control element 70 (Zoom (+)). The processor 122 may also change "→Next App ($A_3$)" to "→Next App ($A_4$)" and "Last App ($A_1$)←" to "Last App ($A_2$)←" in the augmented reality user interface 42. Of course other arrangements/configurations of the augmented reality user interface 42, first user interface 14 and second user interface 15 other than those described are included in the augmented reality visualization system 1.

In an embodiment of the present invention, the augmented reality user interface 42 may not be directly overlaid on the first user interface 14 but may be overlaid on an image (not shown) of the first user interface 14 taken by the camera system 3.

In another embodiment according to the present invention, the first user interface 14 is the footswitch/foot pedal 16, the second interface is a control panel of a treatment center or predetermined functions of a treatment center and an augmented reality glass/smart glass may provide an the augmented reality user interface 42 wherein the footswitch/foot pedal 16, control panel of the treatment center or predetermined functions of a treatment center and augmented reality glass are paired with each other to form an augmented reality visualization system.

Computer System for Controlling a Machine

Having described the augmented reality visualization system 1, reference will now be made to FIG. 3, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the disclosure using other computer systems and/or architectures.

In one example embodiment herein, the computer system 100 may include at least one computer processor 122 and may include a tracking system 2, user interface 126 and input unit 130. The first user interface 14 and second user interface 15 may be part of the computer system 100 or may be separate from the computer system. In one example, a display unit 128, an input unit 130, and the computer processor 122 may collectively form the user interface 126.

The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive a request displaying an augmented reality user interface 42 and may obtain instructions concerning the request from one or more storage units of the computer system 100. The processor 122 may then load said instructions and execute the loaded instructions such as routing augmented reality user interface 42 to a screen of the display device 12 such that the augmented reality user interface 42 is overlaid on the first user interface 14 and such that said augmented reality user interface 42 appears directly superimposed on the first user interface 14. In yet another alternative embodiment of the present invention, the computer system may use projection based augmented reality systems wherein, for example, a projector and depth sensors, along with the tracking system 2 and/or markers (e.g. hidden markers on the first user interface 14) may project the augmented reality user interface 42 directly onto the first user interface 14. Herein, a display 12 such as augmented reality glasses may not be needed to view the augmented reality user interface 42.

Figure 4:
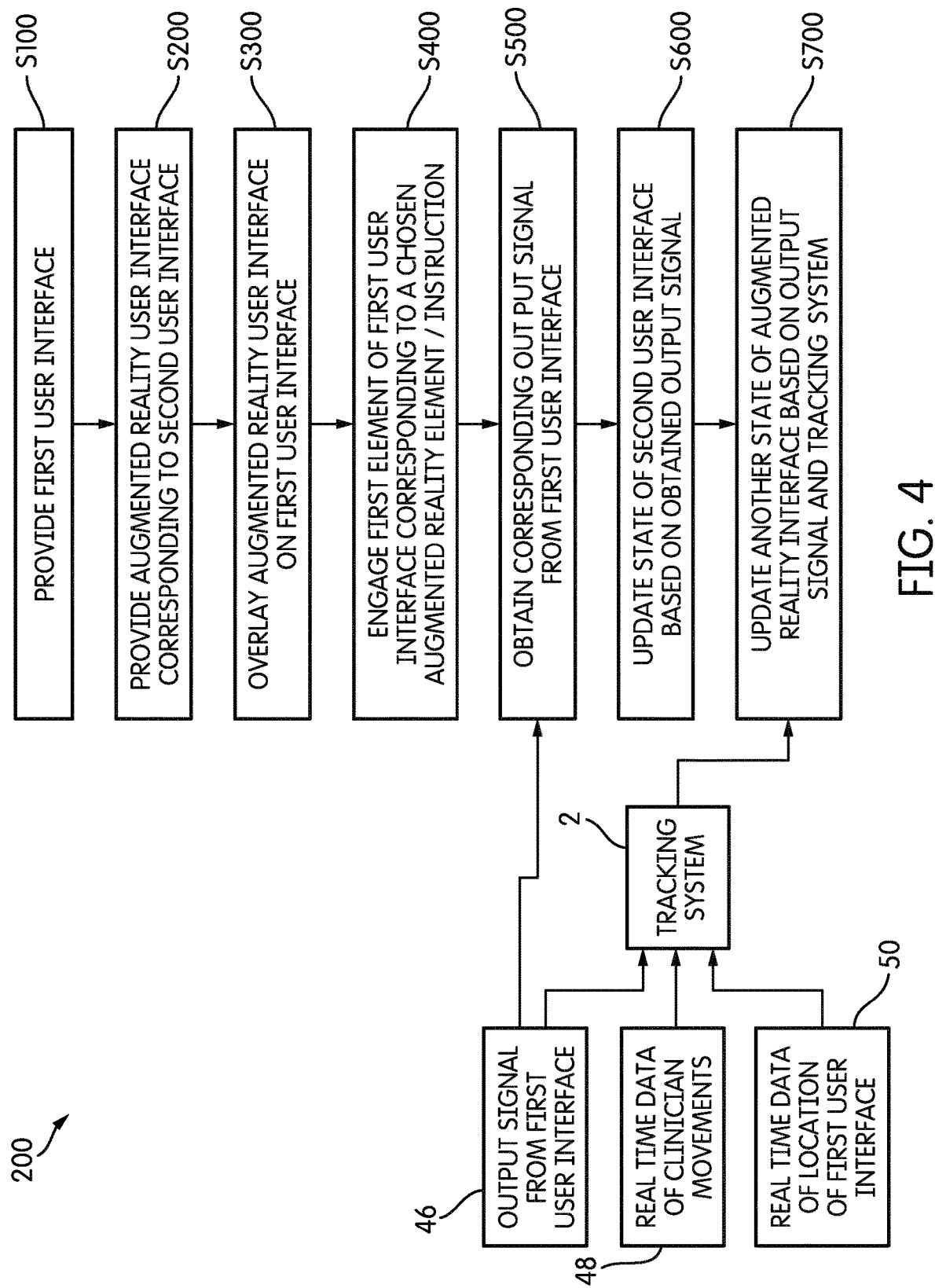
FIG. 4 is a flow chart showing a method according to an exemplary embodiment of the present invention.

One or more steps/procedures may be stored on a non-transitory storage device in the form of computer-readable program instructions. To execute a procedure, the processor 122 loads the appropriate instructions, as stored on a storage device, into memory and then executes the loaded instructions as shown in FIG. 4 which is discussed hereinafter.

The computer system 100 may further comprise a main memory 132, which may be a random access memory ("RAM") and also may include a secondary memory 134.

The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or a wireless interface), a communications port (e.g., a Universal Serial Bus ("USB") port or a FireWire® port), a Personal Computer Memory Card International Association ("PCMCIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described hereinafter.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the augmented reality visualization system 1, to perform all or some of the some of the methods described herein.

Implementation of other hardware arrangement so as to perform the functions described herein will be apparent to persons skilled in the relevant art(s) in view of this description.

Method of Controlling a Machine.

Figure 3:
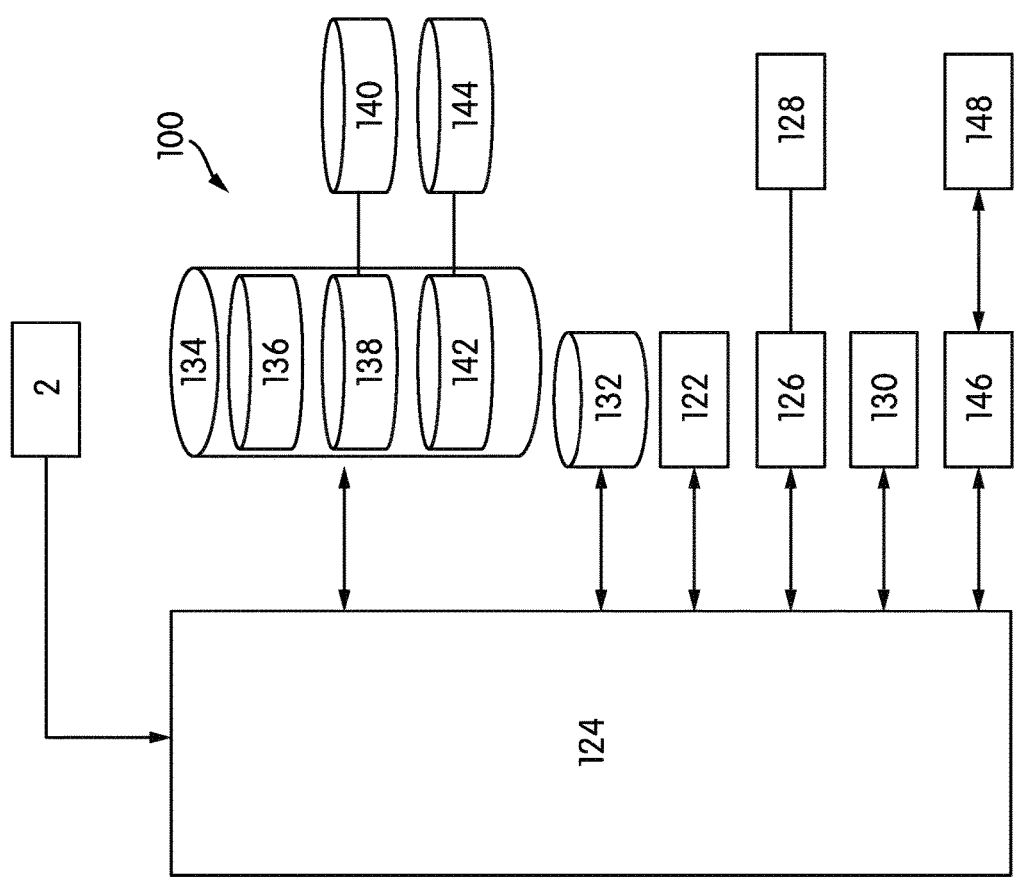
FIG. 3 illustrates a block diagram showing a computer system according to an exemplary embodiment of the present invention.

Having described the computer system 100 of FIG. 3, methods for controlling a machines such as a dental machine will now be further described in conjunction with FIG. 4 which shows a flow chart of a process 200 for controlling a dental machine. The process may start by providing a first user interface 14 as shown in Step S100. The augmented reality user interface 42 may then be provided in Step S200 wherein said augmented reality interface 42 correspond to a second user interface 15 (or wherein augmented reality control elements 70 of the augmented reality interface 42 correspond to second control elements 60 of the second interface 15). The augmented reality user interface 42 may then be overlaid in Step S300 on the first user interface such that augmented reality control elements 70 correspond to first control elements 80 of the first user interface 14 (or to the plurality of positions of a first control element 80 of the first user interface 14 in the case of a foot switch 16). In Step S400, the first control element 80 may be engaged to produce an output/control signal 46 that may correspond to an augmented reality control element 70. Said output/control signal 46 may be obtained in Step S500 and the second user interface 15 may be updated in Step S600 based on the obtained output/control signal 46. For example, an image displayed on the second user interface 15 may be zoomed into, a collection of CBCT images of a patient may be scrolled through, etc. based on the output/control signal 46. As shown in Step S700 using data from the tracking system 2 including, for example, (i) real time data tracking movements of the clinician 48 (ii) real time data tracking a location of the first user interface 14 and/or (iii) output/control signals 46 of the first user interface 14, the augmented data routed to the display device 12 may be dynamically updated in real time for overlay on the first user interface 14 such that the augmentation appears directly superimposed on said first user interface 14 and such that the augmentation is continuously updated when the first control element 80 of the first user interface 14 is engaged.

In an exemplary embodiment of the present invention, the first user interface 14 may be configured to switch between (i) a first set of operations wherein the first user interface 14 controls operations for which it was originally designed for and (ii) a second set of operations for which it was not originally designed for. It may also be configured to switch between any number of predetermined sets of operations. In yet another embodiment of the present invention, any of the sets of operations of the first user interface may be determined by the clinician 10.

In view of the foregoing description, it may be appreciated that the example embodiments described herein provide a method, system and computer readable storage media for controlling a machine such as a dental machine.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

The invention claimed is:

1. A computer-implemented method of utilizing augmented visualization for controlling dental machines, the method comprising:
providing a first user interface, wherein the first user interface comprises a footswitch;
providing a second user interface different from the first user interface, wherein the first user interface and the second user interface comprise physical or graphical elements that allow an interaction between the dental machine and the user:
providing an augmented reality user interface configured to functionally correspond to the second user interface, the first user interface being adapted to transmit one or more control signals functionally corresponding to the augmented reality user interface;
overlaying the augmented user reality interface on a (i) first user interface or on a (ii) a stereoscopic video/projection of the first user interface such that the augmented reality user interface appears to be directly superimposed on the first user interface; and
controlling the second user interface through the said one or more control signals of the first user interface.

2. The method according to claim 1, further comprising overlaying the augmented reality user interface on the first user interface such that one or more augmented reality control elements of the augmented reality user interface functionally correspond to one or more first control elements of the first user interface or also to one or more positions of the first control element of the first user interface and such that the augmented reality user interface appears directly superimposed on the first user interface.

3. The method according to claim 2, wherein the one or more augmented reality control elements of the augmented reality user interface also functionally correspond to one or more second control elements of the second user interface.

4. The method according to claim 1, further comprising; updating the augmented reality user interface based on data selected from the group consisting of (i) real time data tracking clinician movements (ii) real time data tracking a location of the first user interface and (iii) one or more control signals of the first user interface.

5. A system comprising a dental machine for utilizing augmented visualization, comprising:
   a display device for augmented visualization;
   a first user interface, wherein the first user interface comprises a footswitch;
   a second user interface different form the first interface, wherein the first user interface and the second user interface comprise physical or graphical elements that allow an interaction between the dental machine and the user; and
   at least one processor configured to perform the steps of the method according to claim 1.

6. The system according to claim 5, further comprising a tracking system configured to offer real-time position data for a precise location and orientation of objects in a common coordinate system.

7. The system according to claim 6, wherein the tracking system is sensor based and/or vision based.

8. The system according to claim 6, wherein the one or more second control elements of the second user interface include, action items, software applications, videos and/or, images.

9. A non-transitory computer-readable storage medium storing a program which, when executed by a computer based system according to claim 5, causes the computer based system to perform the method according to claim 1.

* * * * *